US006888632B2

(12) United States Patent
Smith

(10) Patent No.: US 6,888,632 B2
(45) Date of Patent: May 3, 2005

(54) MODULATED SCATTEROMETRY

(75) Inventor: Walter Lee Smith, Danville, CA (US)

(73) Assignee: Therma-Wave, Inc., Fremont, CA (US)

( * ) Notice: Subject to any disclaimer, the term of this patent is extended or adjusted under 35 U.S.C. 154(b) by 117 days.

(21) Appl. No.: 10/376,750

(22) Filed: Feb. 28, 2003

(65) Prior Publication Data

US 2004/0169859 A1 Sep. 2, 2004

(51) Int. Cl.[7] ................................................ G01J 4/00
(52) U.S. Cl. ..................................................... 356/369
(58) Field of Search ........................... 356/237.1–237.5, 356/364–370

(56) References Cited

U.S. PATENT DOCUMENTS

| 4,579,463 | A | 4/1986 | Rosencwaig et al. .......... 374/57 |
| 4,632,561 | A | 12/1986 | Rosencwaig et al. ....... 356/432 |
| 4,636,088 | A | 1/1987 | Rosencwaig et al. .......... 374/5 |
| 4,652,757 | A | 3/1987 | Carver ..................... 250/360.1 |
| 4,854,710 | A | 8/1989 | Opsal et al. ................. 356/432 |
| 5,607,800 | A | 3/1997 | Ziger ............................. 430/8 |
| 5,666,200 | A | 9/1997 | Drevillon et al. ............ 356/368 |
| 5,739,909 | A | 4/1998 | Blayo et al. ................. 356/369 |
| 5,867,276 | A | 2/1999 | McNeil et al. ............... 356/445 |
| 5,963,329 | A | 10/1999 | Conrad et al. ............... 356/372 |
| 5,978,074 | A | 11/1999 | Opsal et al. ................... 356/72 |
| 6,151,119 | A | 11/2000 | Campion et al. ............ 356/381 |
| 6,429,943 | B1 | 8/2002 | Opsal et al. ................. 356/625 |
| 6,432,729 | B1 | 8/2002 | Mundt et al. ................... 438/8 |
| 6,451,621 | B1 | 9/2002 | Rangarajan et al. .......... 438/14 |
| 6,535,285 | B1 | * | 3/2003 | Opsal et al. ................. 356/369 |
| 6,583,876 | B2 | * | 6/2003 | Opsal et al. ................. 356/369 |
| 6,660,543 | B1 | 12/2003 | Stirton et al. ................. 438/16 |
| 2002/0151092 | A1 | 10/2002 | Li et al. ....................... 438/16 |
| 2002/0158193 | A1 | 10/2002 | Sezginer et al. ............ 250/237 |

FOREIGN PATENT DOCUMENTS

WO          WO 02/27288 A1     4/2002         ............. G01J/3/28

OTHER PUBLICATIONS

Z.L. Wu, et al., "Laser modulated scattering as a nondestructive evaluation tool for defect inspection in optical materials for high power laser applications", Optics Express, Nov. 9, 1998, vol. 3, No. 10, pp. 376–383.

Z.L. Wu, et al., "Laser modulated scattering as a nondestructive evaluation tool for optical surfaces and thin film coatings", SPIE vol. 3578, Sep.–Oct. 1998.

U.S. Appl. No. 10/339,147 filed Jan. 9, 2003.

M.E. Lee et al., "Analysis of Reflectometry and Ellipsometry Data from Patterned Structures," *AIP Conference Proceedings*, vol. 449 (1998), pp. 331–335.

* cited by examiner

Primary Examiner—Michael P. Stafira
(74) Attorney, Agent, or Firm—Stallman & Pollock LLP

(57) ABSTRACT

An apparatus for scatterometry measurements is disclosed. The apparatus includes a modulated pump source for exciting the sample. A separate probe beam is directed to interact with the sample and the modulated optical response is measured. The measured data is subjected to a scatterometry analysis in order to evaluate geometrical sample features that induce light scattering.

9 Claims, 1 Drawing Sheet

MODULATED SCATTEROMETRY

TECHNICAL FIELD

The subject invention relates to an improved scatterometry system which includes a modulated excitation source and a phase synchronous detection system to provide enhanced measurement capabilities.

BACKGROUND OF THE INVENTION

Over the past several years, there has been considerable interest in using optical scatterometry (i.e., optical diffraction) to perform measurements associated with semiconductor fabrication. One area of great interest has been the critical dimension (CD) measurements of the lines and structures included in integrated circuits. Optical scatterometry has been used to analyze periodic two-dimensional structures (e.g., line gratings) as well as three-dimensional structures (e.g., patterns of vias or mesas). Scatterometry is also used to perform overlay registration measurements. Overlay measurements attempt to measure the degree of alignment between successive lithographic mask layers. (See, U.S. 2002/0158193, incorporated by reference) Scatterometry measurements have also been proposed for monitoring etching, dishing, planarity of a polished layer, control of gate electrode profiles, film stack fault detection, stepper control, deposition process control and resist thickness control. See for example, U.S. Pat. Nos. 6,464,563; 6,451,700; 6,433,871; 6,458,610; 6,479,200; 6,383,824; 6,458,605 and 6,451,621, incorporated herein by reference. The assignee herein has also proposed to use scatterometry analysis to directly measure ion implantation structures. (See, U.S. patent application Ser. No. 10/339,147, filed Jan. 9, 2003-TWI 21800, incorporated herein by reference).

Various optical techniques have been used to perform optical scatterometry. These techniques include broadband scatterometry (U.S. Pat. Nos. 5,607,800; 5,867,276 and 5,963,329), spectral ellipsometry (U.S. Pat. No. 5,739,909) as well as spectral and single-wavelength beam profile reflectance and beam profile ellipsometry (U.S. Pat. No. 6,429,943). In addition it may be possible to employ single-wavelength laser BPR or BPE to obtain CD measurements on isolated lines or isolated vias and mesas (see, U.S. patent application Ser. No. 10/243,245, filed Sep. 13, 2002). Each of these documents are incorporated herein by reference.

Each of these prior techniques use a non-intensity modulated probe beam and the DC scattering is measured. The prior art also includes discussions of measuring light scattered from a sample that has been periodically excited. One such disclosure appears in U.S. Pat. No. 4,632,561 assigned to the same assignee as herein. In the system disclosed in the latter patent, scattered light was used to evaluate subsurface features of the sample such as material composition. The apparatus included an annular detector which was configured to measure the light scattered in all directions. The total amount of detected light was used as a direct measure of material composition. It should be understood that in this system, no effort was made to evaluate the sample based on how the physical structure diffracted light into different orders. Rather, the effort was merely to evaluate the overall change of reflectivity of the sample as expressed in the scattered light signal.

In contrast, optical "scatterometry" attempts to evaluate the geometry of a sample based on the pattern of the diffracted light. More specifically, scatterometry systems use a modeling approach to transform scatterometry measurements into geometric measurements. For this type of approach, a theoretical model is defined for each physical structure that will be analyzed. The theoretical model predicts the empirical measurements (scatterometry signals) that scatterometry systems would record for the structure. A rigorous coupled wave theory can be used for this calculation. The theoretical results of this calculation are then compared to the measured data (typically in normalized form). To the extent the results do not match, the theoretical model is modified and the theoretical data is calculated once again and compared to the empirical measurements. This process is repeated iteratively until the correspondence between the calculated theoretical data and the empirical measurements reaches an acceptable level of fitness. At this point, the characteristics of the theoretical model and the physical structure should be very similar.

Evaluation of the theoretical models is a complex task, even for relatively simple structures. As the models become more complex (particularly as the profiles of the walls of the features become more complex) the calculations can become extremely time consuming. Even with high-speed processors, real-time evaluation of these calculations can be difficult. Analysis on a real-time basis is very desirable so that manufacturers can immediately determine when a process is not operating correctly. The need is becoming more acute as the industry moves towards integrated metrology solutions wherein the metrology hardware is integrated directly with the process hardware.

A number of approaches have been developed to overcome the calculation bottleneck associated with the analysis of scatterometry results. Many of these approaches have involved techniques for improving calculation throughput, such as parallel processing techniques. An approach of this type is described in a co-pending application PCT WO 03/009063 (incorporated by reference) which describes distribution of scatterometry calculations among a group of parallel processors.

Another approach is to use pre-computed libraries of predicted measurements. This type of approach is discussed in U.S. Pat. No. 6,483,580 (Xu), incorporated herein by reference. In this approach, the theoretical model is parameterized to allow the characteristics of the physical structure to be varied. The parameters are varied over a predetermined range and the theoretical result for each variation to the physical structure is calculated to define a library of solutions. When the empirical measurements are obtained, the library is searched to find the best fit.

In a variation on this approach, the library data is used as a starting point and an estimation or interpolation algorithm is used to refine the results. U.S. Pat. No. 5,867,276 describes a system of training a library to permit linear estimations of solutions. Another form of interpolation can be found in U.S. patent application Ser. No. 2002/0038196, published Mar. 28, 2002. This use of interpolation avoids the penalty associated with generating results in real-time, but may sacrifice accuracy during the interpolation process. Any of these approaches could be used with the subject invention.

SUMMARY OF THE INVENTION

The subject invention is directed to an improvement in prior scatterometry systems. As used herein, scatterometers include a source of light which defines a probe beam that is used to illuminate the sample. The light reflected and diffracted from the sample is measured. In many current systems, the measured light is primarily zeroth order, but higher orders could also be measured. The results are then analyzed by comparing the empirical signal to a signal that would be predicted from a theoretical model using an electromagnetic wave analysis. The most common wave analysis used for this purpose is rigorous coupled wave theory, however, various other approaches are available including Green's functions and finite difference methods.

In order to improve the measurement sensitivity and possibly permit measurements with higher spatial resolution, it is proposed that the sample be periodically excited with an intensity modulated pump beam. The pump beam can be a beam of electromagnetic radiation, but can also be a particle beam or acoustic field. The modulation frequency selected depends on the sample, but could range from a few hertz to the gigahertz range. Most typically, the modulation frequency would be in the kilohertz or megahertz ranges.

The probe beam would then be directed to overlap at least a portion of the area which is being periodically excited. The output of the detector would be processed in a manner to extract the modulated portion of the signal induced by the pump source. Such processing can be performed with lock-in detectors as discussed below.

The processed signal would then be subjected to an analysis of the type now used for scatterometry measurements. In this way, information about critical dimensions and other features could be determined. Such information can be derived from any layer in a stack. The use of the modulated pump beam (or other modulator) can provide improved signal-to-noise performance in the scatterometry.

It should be understood that this analysis is completely different from the modulated scattering experiments discussed above where the scattered signal was simply used as measure of the change in reflectance of the sample. In contrast, the subject analysis attempts to determine the geometrical structure of the surface actually causing the light to diffract.

It may also be possible to use this approach to improve the spatial resolution of the measurement. For example, many existing scatterometers use a broadband source to generate a polychromatic probe beam. Measurements are taken as a function of wavelength. Unfortunately, it is difficult to focus a polychromatic probe beam to the extremely small spot sizes desired by the semiconductor industry. On the other hand, a narrow wavelength beam from a laser can be focused to significantly smaller spot. A beam from a laser could be modulated and used as the pump beam and focused to spot size well within the spot size of the polychromatic probe beam spot. The phase synchronous detection of the scattered light would then correspond to the information generated from the much smaller region illuminated by the pump source. In this way, the spatial resolution could be enhanced while still permitting detection at multiple wavelengths.

Use of a normal incidence, tightly focused pump beam can also improve the performance of an off-axis ellipsometer based scatterometer. As noted above, scatterometers systems can have an ellipsometer configuration where the probe beam is directed to the sample at a non-normal angle of incidence. Such an orientation causes the spot size of the beam to elongate. As noted above, by using a tightly focused modulated pump beam, the spatial resolution of the measurement can be enhanced. Beyond that, the normal incidence pump beam can be used to illuminate narrow open structures such as contact holes or vias.

While the subject concept can be used with unpolarized light, polarized light configurations are also possible. For example, either or both of the beams can be polarized. The polarization axis of the pump and probe beam could be the same or perpendicular.

Beyond specific physical geometries, diffracting structures created by the stoichiometry of the sample can be measured. For example, periodic patterns of implanted regions could be monitored.

The subject method could be used for measuring characteristics of semiconductor films such as (but not limited to) Si, GaAs, InP, etc., wherein the pump beam may generate electrons and holes and thereby enable certain desired quantities to be better measured, such as (but not limited to) ion-implantation dose or ion implantation depth (junction depth) or ion implantation lateral profile (shape as a function of x, y, z within patterned features on a semiconductor wafer either before any annealing step or after an annealing process.

The subject method could be used for measuring characteristics of films and substrates such as (but not limited to) thickness, critical dimensions, pattern registration ("overlay"), carrier mobility, junction depth and depth profile, implantation and carrier lateral profile, plasma damage depth and profile, advanced substrate (SOI, SiGe, strained Si) characteristics such as doping depth, profile and profile abruptness, interface abruptness and uniformity, erosion or dishing in CMP structures.

The subject system could be used in a configuration as described above with a modulated pump beam and a scatterometric probe beam, combined with a laser (single-wavelength) probe beam in order to offer the same modes of operation as assignee's commercial Therma-Probe, operating to measure modulated reflectance, (disable or ignore the scatterometric probe beam) plus the modulated scatterometric mode taught herein (with the scatterometric probe beam active and the laser probe disabled or ignored optionally). Information about the assignee's modulated optical reflectivity systems can be found in U.S. Pat. Nos. 4,579,463; 4,636,088; 4,854,710 and 5,987,074, each of which is incorporated herein by reference.

The subject system could be used to isolate the measurement to a particular film layer within a multi-layer stack, by arranging the pump beam to be absorbed selectively in that certain layer. This can be advantageous, for example, in a multi-layer interconnect structure comprised of a large plurality of film layers beneath a particular layer of interest, such as the top most layer). This configuration would allow for rejection of signal contribution from other layers in the stack.

The application method disclosed here is independent of the details of the scatterometer apparatus design. Additional background information on scatterometers and scatterometry analysis can be found in the above cited patents and applications.

Further objects and advantages of the subject invention will become apparent from the following detailed description taken in conjunction with the drawings in which:

DETAILED DESCRIPTION OF THE PREFERRED EMBODIMENT

Figure 1:
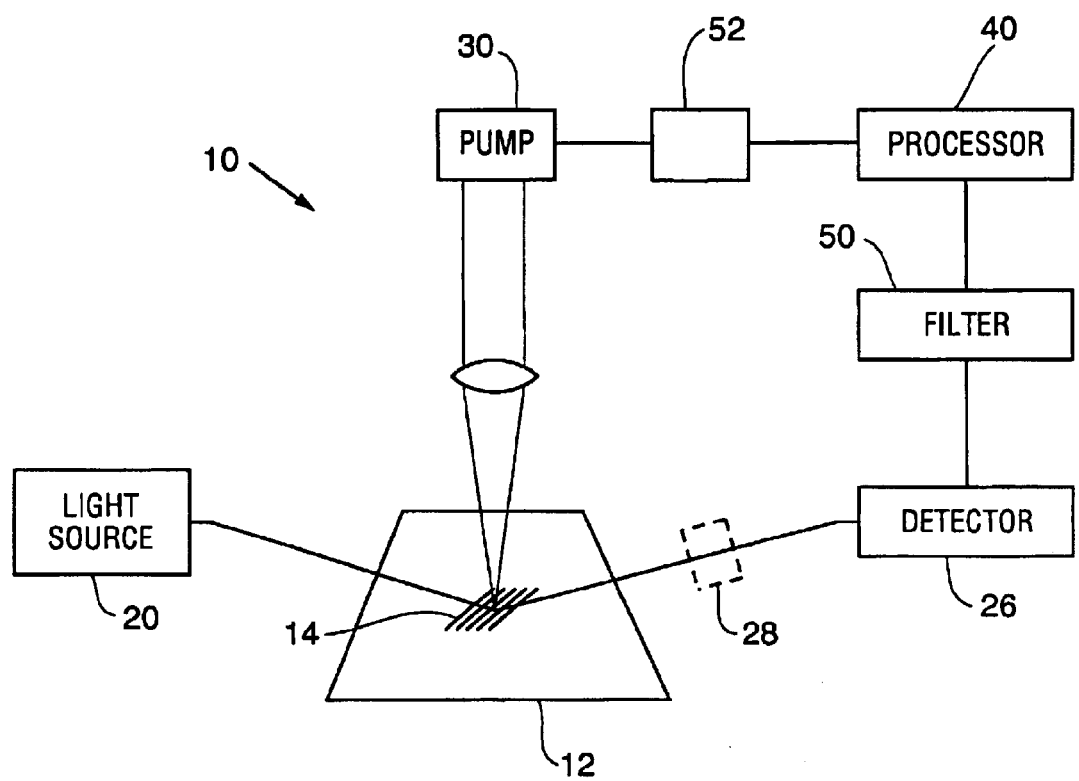
FIG. 1 is a schematic diagram of scatterometry system configured in accordance with the subject invention.

FIG. 1 illustrates a basic form of a scatterometry system 10 of the subject invention. The system 10 is intended to be used to perform evaluations of the type associated with prior scatterometers. For example, scatterometers have been used to evaluate a sample 12 having a periodic pattern of lines 14 formed thereon. The evaluation includes determining features such as height, spacing, side wall angle and shape. As noted above, scatterometers have also been used for to evaluate three dimensional features as well as for monitoring etching, dishing, planarity of a polished layer, control of gate electrode profiles, film stack fault detection, stepper control, deposition process control and resist thickness control The subject scatterometers includes a light source 20 for of generating a probe beam of radiation 22. The light source is typically either a laser or a broad band or white light source for generating a polychromatic probe beam. The probe beam is directed to reflect off the sample 12. The probe beam can be directed either at normal incidence or off-axis. Reflectometers are more conventionally normal incidence devices while ellipsometers are conventionally off-axis device. However, it is also known to operate reflectometers off-axis and ellipsometers in a normal orientation, particularly when measuring anisotropic features such as a periodic line structure.

The reflected/diffracted probe beam is measured by a detector 26. In FIG. 1, detector 26 is shown measuring the zeroth order diffracted light. As is known, higher diffraction orders can be measured. If the system is a reflectometer, detector 26 is configured to measure the intensity of the reflected beam. An array of photodetector elements will be used to measure multiple wavelengths. In an ellipsometer configuration, additional elements such as polarizers and/or compensators (waveplates) are used (as shown generally in phantom as 28) to determine the change in polarization state of the beam induced by the interaction with the sample. Additional examples of spectroscopic reflectometers and ellipsometers suitable for scatterometry analysis can be found in U.S. Pat. Nos. 5,608,526 and 5,798,837 incorporated herein by reference.

In state of the art scatterometers, the normalized output of the detector would be compared with theoretical data determined from a theoretical model. The processing can proceed with an iterative analysis to find a best fit solution. Alternatively, the measurements can be compared to a library of solutions, each solution associated with a different structure. Details of these types of analyses are set forth in the above patents and will not be repeated herein. However, the goal is to determine the geometrical characteristics of the sample that contribute to the scattering signal. (Additional references describing scatterometry analysis include U.S. patent application Ser. No. 10/212,385, filed Aug. 5, 2002 and relates to using Green's functions to predict the electrical field and U.S. patent application Ser. No. 10/345,814, filed Jan. 16, 2003 which relates to predicting the electrical fields using a finite difference method. Both of the applications are incorporated herein by reference.)

In accordance with the subject invention, the signal collection is improved by using a modulated detection scheme. In this scheme, a pump source 30 is used to generate a pump beam 32 to excite the sample. Pump source may be an intensity modulated laser or incoherent light source. Gas, solid state or semiconductor lasers can be used. Other means for exciting the sample can include different sources of electromagnetic radiation or particle beams such as from an electron gun. The pump source induces a modulation on the optical characteristics of the sample, including reflectivity or electrical conduction parameters (e.g. mobility) which exhibit behavior which is coupled to optical properties.

A lens 34 can be used to focus the pump beam onto the sample. As noted above, it would be possible to tightly focus the pump beam to a spot size much smaller than the probe beam spot size. In this manner, the spatial resolution of the measurement can be improved.

The pump source output is controlled by processor 40. As noted above, the pump beam is intensity modulated at a predetermined frequency, selected depending upon the desired measurement. In order to detect the modulated optical scattered signal (MOS), the output of the photodetector 26 is passed through a filter 50 before reaching processor 40. One function of filter 50 is to pass a signal to the processor 40 proportional to the DC power of the reflected probe. A portion of filter 50 also functions to isolate the changes in power of the reflected probe beam which are synchronous with the pump beam modulation frequency. In the preferred embodiment, the filter 50 includes a lock-in detector for monitoring the magnitude and phase of the periodic reflectivity signal. Because the modulation frequency of pump laser can be so high, it is preferable to provide an initial down-mixing stage for reducing the frequency of detection. (See U.S. Pat. No. 5,978,074 for more details of a synchronous detection system.)

In the preferred embodiment, a frequency synthesizer 52 is provided for generating the various pump beam modulation frequencies. Synthesizer 52 is under the control of processor 40. The output of the synthesizer is delivered as a signal to the power supply of pump source 30.

Synthesizer 52 also generates an electronic heterodyne signal for delivery to the lock-in amplifier of filter 50. The heterodyne signal will be close to, but different from the signal sent to the pump source. The heterodyne signal from the synthesizer is combined with the output from the signal detector 26 in a mixer (not shown). The output of the mixer will include signal components at both the sum and difference of the two input signals. The difference signal will be at the relatively lower frequency than the modulation frequency. All the signals are passed through a low pass filter to eliminate the high frequency components from the synthesizer and the detector. The low frequency signal is then demodulated by demodulator. The outputs of demodulator are the "in phase" and "quadrature" signals typical of a lock-in amplifier. The in-phase and quadrature signals can be used by processor 40 to calculate the magnitude and the phase of the modulated optical scatterometry signal.

As an alternative to using an electronic heterodyne downmixing system, it is also possible to reduce the frequency of detection using an optical heterodyne approach. Such an optical approach is disclosed in U.S. Pat. No. 5,408,327, incorporated herein by reference. In the latter system, both the pump beam and the probe beam are modulated but at slightly different frequencies. The probe beam picks up the modulation induced by the pump beam. This modulated optical scatter signal picked up upon reflection "mixes" with the inherent modulation of the probe beam, creating additional modulations in the beam at both the sum and difference frequency. This process is analogous to electrical heterodyning. The difference or "beat" frequency is much lower than either of the initial beam modulation frequencies and can therefore be detected by a low frequency lock-in amplifier.

To insure proper repeatability of the measurements, the signals must be normalized in the processor. As noted above, the DC reflectivity of the probe beam is derived from detector 26. In addition, the DC output powers of the pump and probe beams will be monitored by incident power detectors (not shown). The outputs of the incident power detector are supplied to the processor 40.

The signals can be further normalized by taking a measurement of the power of the pump beam 32 after it has been reflected. This measurement is used to determine the amount of pump energy which has been absorbed in the sample. The DC signal for both the incident pump and probe beam powers as well as the reflected beam powers are used to correct for light source fluctuations and absorption and reflection variations in the samples. In addition, the signals can be used to help calculate sample parameters.

Once the normalized signals are obtained, they can be subjected to a scatterometry analysis to evaluate the features of the sample. As noted above, one approach is to evaluate the measurements in real time. In this approach, a mathematical model of the sample is created. A best guess of sample parameters is assigned to the model and the optical response of a structure having those selected parameters is calculated. Such calculations are performed using, for example, rigorous coupled wave theory or other frameworks such as Green's functions or finite difference approximations. (See, the U.S. patent applications cited above). The calculations will depend upon the type of measurement used, e.g. reflectometry or ellipsometry (or both). The calculated optical response is compared to the measured optical response. Any deviations between the calculated optical response and the measured optical response are used to vary the initial starting parameter guesses and the process is repeated in an iterative fashion until satisfactory convergence is reached.

It is also well known to create libraries of signatures associated with various possible geometries. A measured signaled can then be compared to the library to determine the geometry of the sample.

It may also be desirable to combine the modulated scatterometry measurement with a conventional non-modulated measurement. More specifically, the probe beam could be monitored during a period when the pump modulation source is turned off. The resulting measurement could be combined with the modulated measurement to further refine the analysis of the sample.

While the subject invention has been described with reference to a preferred embodiment, various changes and modifications could be made therein, by one skilled in the art, without varying from the scope and spirit of the subject invention as defined by the appended claims.

I claim:

1. An apparatus for evaluating a sample have light diffracting features comprising:

an intensity modulated energy source for periodically exciting the sample;

a probe beam directed to reflect off the sample in the region which has been periodically excited;

a detector for monitoring the probe beam after interaction with the sample and generating output signals; and a processor for filtering the output signals to determine the modulated optical scattering of the light and wherein the modulated optical scattering response is analyzed according to a scatterometry analysis to evaluate the light diffracting features on the sample.

2. An apparatus as recited in claim 1 wherein said probe beam is polychromatic and detector generates output signals as a function of wavelength.

3. An apparatus as recited in claim 2 wherein the detector and processor operate as a reflectometer.

4. An apparatus as recited in claim 2 further including an analyzer and wherein the processor determines the change in polarization state of the probe beam.

5. A method for evaluating a sample have light diffracting features comprising the steps of:

periodically exciting a region on the sample;

directing a probe beam of radiation to reflect off a portion of the region which has been periodically excited;

monitoring the probe beam after interaction with the sample and generating output signals; and filtering the output signals to determine the modulated optical scattering of the light and wherein the modulated optical scattering response is analyzed according to a scatterometry analysis to evaluate the light diffracting features on the sample.

6. A method as recited in claim 5 wherein said probe beam is polychromatic and the output signals are generated as a function of wavelength.

7. A method as recited in claim 6 wherein the monitoring and filtering step measure the modulated changes in the intensity of the probe beam.

8. A method as recited in claim 6 wherein the monitoring and filtering step determines the modulated changes in polarization state of the probe beam.

9. A method as recited in claim 5 further including the step monitoring the probe beam after interaction with the sample during a period when the sample is not being periodically excited and using the results to further evaluate the sample.

* * * * *